United States Patent
Hossack et al.

(10) Patent No.: US 9,492,140 B2
(45) Date of Patent: Nov. 15, 2016

(54) DEVICES, SYSTEMS, AND METHODS FOR FORWARD LOOKING IMAGING

(71) Applicant: Volcano Corporation, San Diego, CA (US)

(72) Inventors: Norman H. Hossack, Folsom, CA (US); Andy Gerhardt, Sacramento, CA (US)

(73) Assignee: Volcano Corporation, San Diego, CA (US)

( * ) Notice: Subject to any disclaimer, the term of this patent is extended or adjusted under 35 U.S.C. 154(b) by 142 days.

(21) Appl. No.: 13/915,192

(22) Filed: Jun. 11, 2013

(65) Prior Publication Data

US 2013/0331706 A1    Dec. 12, 2013

Related U.S. Application Data

(60) Provisional application No. 61/658,748, filed on Jun. 12, 2012.

(51) Int. Cl.
| | |
|---|---|
| *A61B 8/14* | (2006.01) |
| *A61B 8/12* | (2006.01) |
| *A61B 5/00* | (2006.01) |
| *A61B 8/00* | (2006.01) |

(52) U.S. Cl.
CPC ........... *A61B 8/12* (2013.01); *A61B 5/445* (2013.01); *A61B 8/4461* (2013.01)

(58) Field of Classification Search
USPC .......................................................... 600/467
See application file for complete search history.

(56) References Cited

U.S. PATENT DOCUMENTS

| | | | | |
|---|---|---|---|---|
| 4,951,677 | A * | 8/1990 | Crowley et al. | 600/463 |
| 5,038,789 | A * | 8/1991 | Frazin | 600/471 |
| 5,190,045 | A * | 3/1993 | Frazin | 600/463 |
| 5,201,315 | A * | 4/1993 | Griffith | 600/467 |
| 5,373,845 | A * | 12/1994 | Gardineer et al. | 600/445 |
| 5,640,961 | A * | 6/1997 | Verdonk | 600/459 |
| 5,690,117 | A * | 11/1997 | Gilbert | 600/463 |
| 5,704,361 | A * | 1/1998 | Seward et al. | 600/459 |
| 5,771,895 | A * | 6/1998 | Slager | 600/462 |
| 6,050,949 | A * | 4/2000 | White et al. | 600/466 |
| 6,200,269 | B1 * | 3/2001 | Lin et al. | 600/466 |
| 6,241,744 | B1 * | 6/2001 | Imran et al. | 606/159 |
| 6,296,608 | B1 * | 10/2001 | Daniels et al. | 600/104 |
| 6,315,732 | B1 * | 11/2001 | Suorsa et al. | 600/466 |
| 6,585,657 | B2 * | 7/2003 | Yock | 600/467 |
| 6,702,750 | B2 * | 3/2004 | Yock | 600/467 |
| 7,155,272 | B2 * | 12/2006 | Yamaguchi et al. | 600/425 |
| 7,335,180 | B2 * | 2/2008 | Nita et al. | 604/22 |
| 8,449,468 | B2 * | 5/2013 | Petersen et al. | 600/467 |

(Continued)

OTHER PUBLICATIONS

International Search Report and Written Opinion received in Patent Cooperation Treaty Application No. PCT/US2013/045400, dated Feb. 21, 2014, 10 pages.

*Primary Examiner* — James Kish
(74) *Attorney, Agent, or Firm* — Haynes and Boone, LLP

(57) ABSTRACT

Devices, systems, and methods for forward looking imaging are provided. A system for imaging a vessel of a patient comprises an elongated sheath having a proximal and a distal end. The sheath includes a flexible body with a first lumen in communication with a distal opening at the distal end. The system further comprises an imaging core disposed within the first lumen. The imaging core includes a transducer subassembly sized to extend within the first lumen. The transducer subassembly is adapted to transmit a beam, distally of the elongated sheath, through the distal opening.

25 Claims, 7 Drawing Sheets

(56) References Cited

U.S. PATENT DOCUMENTS

| | | | |
|---|---|---|---|
| 8,613,751 B2* | 12/2013 | Nita et al. | 606/169 |
| 8,712,506 B2* | 4/2014 | Courtney et al. | 600/478 |
| 8,801,617 B2* | 8/2014 | McGee | 600/462 |
| 2002/0082503 A1* | 6/2002 | Chandrasekaran et al. | 600/466 |
| 2005/0203396 A1 | 9/2005 | Angelsen et al. | |
| 2005/0272975 A1* | 12/2005 | McWeeney et al. | 600/113 |
| 2007/0167804 A1* | 7/2007 | Park et al. | 600/459 |
| 2008/0167602 A1* | 7/2008 | Nita et al. | 604/22 |
| 2009/0069694 A1* | 3/2009 | Amundson et al. | 600/467 |
| 2009/0088648 A1 | 4/2009 | Jaffe et al. | |
| 2009/0234445 A1 | 9/2009 | Maschke | |
| 2010/0179426 A1* | 7/2010 | Davies et al. | 600/439 |
| 2011/0263986 A1* | 10/2011 | Park et al. | 600/462 |
| 2012/0123271 A1* | 5/2012 | Cai | 600/454 |
| 2012/0197113 A1* | 8/2012 | Courtney et al. | 600/427 |
| 2014/0194744 A1* | 7/2014 | Havel et al. | 600/459 |

\* cited by examiner

DEVICES, SYSTEMS, AND METHODS FOR FORWARD LOOKING IMAGING

CROSS REFERENCE TO RELATED APPLICATIONS

The present application claims priority to and the benefit of U.S. Provisional Patent Application No. 61/658,748, filed Jun. 12, 2012, which is hereby incorporated by reference herein in its entirety.

TECHNICAL FIELD

The present disclosure relates generally to the field of invasive imaging systems, and in particular, to devices, systems, and methods comprising a catheter for forward looking intravascular ultrasound (IVUS) imaging.

BACKGROUND

IVUS imaging is widely used in interventional cardiology as a diagnostic tool for assessing a diseased vessel, such as an artery, within the human body to determine the need for treatment, to guide the intervention, and/or to assess its effectiveness. IVUS imaging uses ultrasound echoes to form a cross-sectional image of the vessel of interest. Typically, the ultrasound transducer on an IVUS catheter both emits ultrasound pulses and receives the reflected ultrasound echoes. The ultrasound waves pass easily through most tissues and blood, but they are partially reflected by discontinuities arising from tissue structures (such as the various layers of the vessel wall), red blood cells, and other features of interest. The IVUS imaging system, which is connected to the IVUS catheter by way of a patient interface module, processes the received ultrasound echoes to produce a cross-sectional image of the vessel where the catheter is located.

There are primarily two types of IVUS catheters in common use today: solid-state and rotational. Solid-state IVUS catheters use an array of ultrasound transducers (typically 64) distributed around the circumference of the catheter and connected to an electronic multiplexer circuit. The multiplexer circuit selects array elements for transmitting an ultrasound pulse and receiving the echo signal. By stepping through a sequence of transmit-receive pairs, the solid-state IVUS system can synthesize the effect of a mechanically scanned transducer element, but without moving parts. Since there is no rotating mechanical element, the transducer array can be placed in direct contact with the blood and vessel tissue with minimal risk of vessel trauma and the solid-state scanner can be wired directly to the imaging system with a simple electrical cable and a standard detachable electrical connector.

In the typical rotational IVUS catheter, a single ultrasound transducer element fabricated from a piezoelectric ceramic material is located at the tip of a flexible driveshaft that spins inside a sheath inserted into the vessel of interest. The typical transducer element is oriented such that the ultrasound beam propagates generally perpendicular to the axis of the catheter. In the typical IVUS catheter, the fluid-filled (e.g., saline-filled) sheath protects the vessel tissue from the spinning transducer and driveshaft while permitting ultrasound signals to freely propagate from the transducer into the tissue and back. As the driveshaft rotates (typically at 30 revolutions per second), the transducer is periodically excited with a high voltage pulse to emit a short burst of ultrasound. The ultrasound is emitted from the transducer, through the saline-fill and sheath wall, in a direction generally perpendicular to the axis of rotation of the driveshaft. The same transducer then listens for the returning echoes reflected from various tissue structures, and the IVUS imaging system assembles a two dimensional image of the vessel cross-section from a sequence of several hundred of these ultrasound pulse/echo acquisition sequences occurring during a single revolution of the transducer.

While existing IVUS catheters deliver useful diagnostic information, there is a need for enhanced image quality to provide more valuable insight into the vessel condition and for enhanced catheter utility such as navigation or delivery of treatment. For further improvement in rotational IVUS imaging, it may be desirable to use a transducer that provides images of vascular regions distal of the IVUS catheter. Additionally, it may be desirable to use a single catheter that provides multiple utilities including imaging, navigation, and treatment delivery. Accordingly, there remains a need for improved imaging devices, systems, and methods.

SUMMARY

The embodiments of the invention are summarized by the claims that follow below.

In one embodiment, a system for imaging a vessel of a patient comprises an elongated sheath having a proximal and a distal end. The sheath includes a flexible body with a first lumen in communication with a distal opening at the distal end. The system further comprises an imaging core disposed within the first lumen. The imaging core includes a transducer subassembly sized to extend within the first lumen. The transducer subassembly is adapted to transmit a beam, distally of the elongated sheath, through the distal opening.

In another embodiment, a method of imaging a vessel of a patient comprises providing an elongated sheath having a proximal and a distal end. The sheath includes a flexible body with a first lumen in communication with a distal opening at the distal end. The method also comprises providing a transducer subassembly disposed within the first lumen and rotating the transducer subassembly within the first lumen while directing a beam from the distal opening. The method further comprises receiving a reflected beam through the distal opening.

Additional aspects, features, and advantages of the present disclosure will become apparent from the following detailed description.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DETAILED DESCRIPTION

Figure 1:
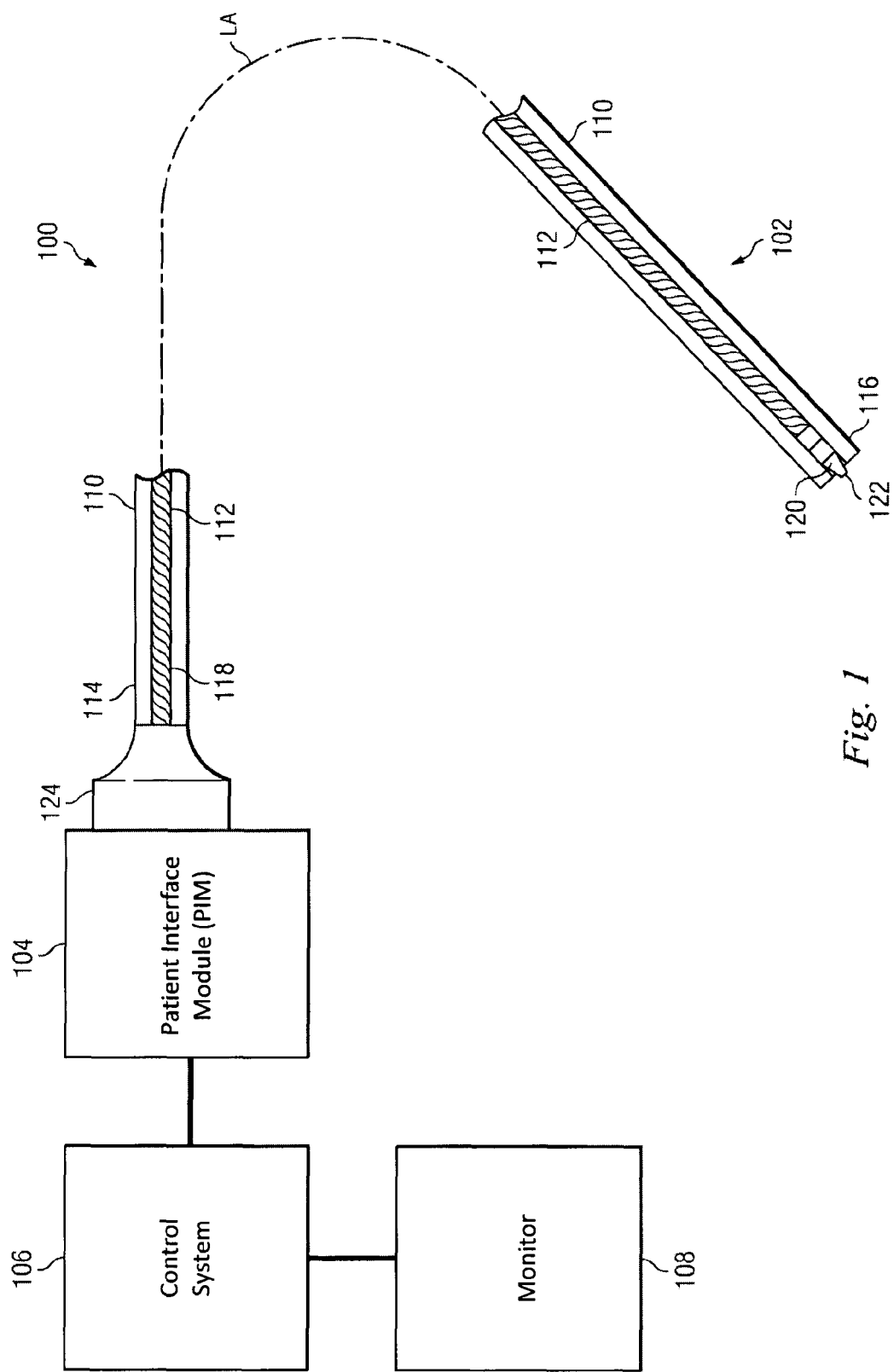
FIG. 1 is a schematic illustration of an IVUS system according to one embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Referring first to FIG. 1, an imaging system 100 for insertion into a patient for diagnostic imaging is shown. The system 100 comprises an IVUS catheter 102 coupled by a patient interface module (PIM) 104 to an IVUS control system 106. The control system 106 is coupled to a monitor 108 for display of an IVUS image.

The IVUS catheter 102 includes an elongated, flexible catheter sheath 110 shaped and configured for insertion into a lumen of a blood vessel (not shown) such that a longitudinal axis LA of the catheter 102 substantially aligns with a longitudinal axis of the vessel at any given position within the vessel lumen. In that regard, the curved configuration illustrated in FIG. 1 is for exemplary purposes and in no way limits the manner in which the catheter 102 may curve in other embodiments. Generally, the catheter 102 may be configured to take on any desired arcuate profile when in the curved configuration.

A rotating imaging core 112 extends within the sheath 110. The sheath 110 has both a proximal end portion 114 and a distal end portion 116. The imaging core 112 has a proximal end portion 118 disposed within the proximal end portion 114 of the sheath 110 and a distal end portion 120 disposed within the distal end portion 116 of the sheath 110.

The distal end portion 116 of the sheath 110 and the distal end portion 120 of the imaging core 112 are inserted into a patient during the operation of the system 100. The usable length of the catheter 102 (e.g., the portion that can be inserted into a patient) can be any suitable length and can be varied depending upon the application.

The proximal end portion 114 of the sheath 110 and the proximal end portion 118 of the imaging core 112 are connected to the interface module 104. The proximal end portions 114, 118 are fitted with a catheter hub 124 that is removably connected to the interface module 104.

The rotation of the imaging core 112 within the sheath 110 is controlled by the interface module 104, which provides a plurality of user interface controls that can be manipulated by a user. The interface module 104 can receive, analyze, and/or display information received through the imaging core 112. It will be appreciated that any suitable functionality, controls, information processing and analysis, and display can be incorporated into the interface module 104.

The distal end portion 120 of the imaging core 112 includes a transducer subassembly 122. The transducer subassembly 122 can be of any suitable type for visualizing a vessel and, in particular, a severe occlusion in a vessel. Accordingly, the transducer subassembly may be an ultrasound transducer array (e.g., arrays having 16, 32, 64, or 128 elements are utilized in some embodiments) or a single ultrasound transducer. In alternative embodiments, one or more optical coherence tomography ("OCT") elements (e.g., mirror, reflector, and/or optical fiber) may be included in or comprise the transducer subassembly. In some embodiments transducer subassembly 122 is configured to be rotated (either by use of a motor or other rotary device or manually by hand) to obtain images of the vessel. Suitable transducer subassemblies may include, but are not limited to, one or more advanced transducer technologies such as Piezoelectric Micromachined Ultrasonic Transducer ("PMUT") and Capacitive Micromachined Ultrasonic Transducer ("CMUT").

In some embodiments, wires associated with the IVUS imaging system 100 extend from the control system 106 to the interface module 104 such that signals from the control system 106 can be communicated to the interface module 104 and/or vice versa. In some embodiments, the control system 106 communicates wirelessly with the interface module 104. Similarly, it is understood that, in some embodiments, wires associated with the IVUS imaging system 100 extend from the control system 106 to the monitor 108 such that signals from the control system 106 can be communicated to the monitor 108 and/or vice versa. In some embodiments, the control system 106 communicates wirelessly with the monitor 108.

Figure 2:
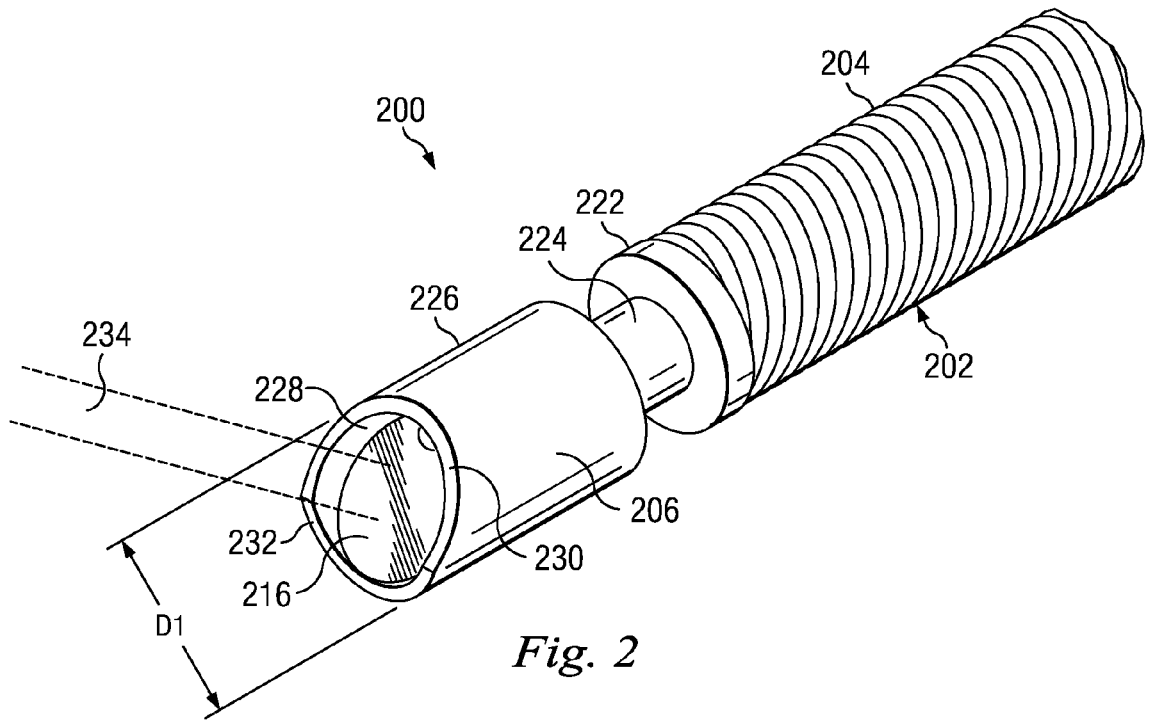
FIG. 2 is an illustration of a distal end of an imaging core according to one embodiment of the present disclosure.
Figure 3:
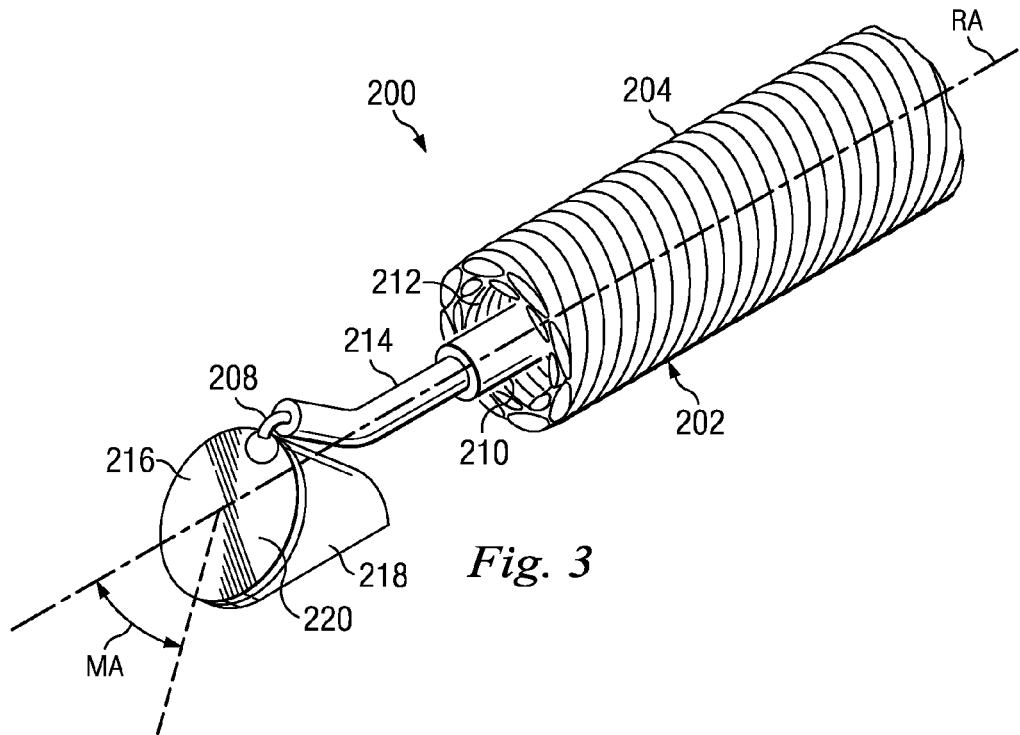
FIG. 3 is an illustration of the distal end of the imaging core of FIG. 2 with a transducer housing assembly omitted to provide an improved view of the transducer subassembly.

FIGS. 2-5 show more detailed views of a distal portion of a rotational IVUS catheter system 200. In some aspects, this catheter may be similar to traditional rotational IVUS catheters, such as the Revolution® catheter system available from Volcano Corporation and described in U.S. Pat. No. 8,104,479, or those disclosed in U.S. Pat. Nos. 5,243,988 and 5,546,948, each of which is hereby incorporated by reference in its entirety. However, in other aspects, the catheter 200 provides forward imaging capability not found in traditional rotational IVUS catheters. As shown in FIGS. 2 and 3, the catheter system 200 includes an imaging core 202. The imaging core 202 includes a flexible drive shaft 204 which may be formed from two or more layers of counter wound stainless steel wires, welded or otherwise secured to a transducer housing 206 such that rotation of the flexible drive shaft 204 imparts rotation to the housing 206.

An electrical cable 208 with optional shielding 210 extends through an inner lumen 212 of the flexible drive shaft 204. The cable 208 further extends past the distal end of the drive shaft 204, through an angled neck 214. The leads of the cable 208 are soldered, welded, or otherwise electrically coupled to a transducer subassembly 216. The proximal end of the cable 208 terminates in a series of rings for electrical interface with an interface module through a hub (similar to hub 124).

The transducer subassembly 216 is secured to the housing 206 by a backing material 218 which may be an epoxy or a similar bonding agent. The backing material 218 also serves to absorb acoustic reverberations within the housing 206 and as a strain relief for the electrical cable 208 where it is attached to the transducer subassembly 216.

The transducer subassembly 216 includes a generally circular or elliptical planar face 220 mounted at an oblique mounting angle MA with respect to a rotational axis RA of the imaging core 202. In one embodiment, the mounting angle MA may be 45°, but larger or smaller mounting angles may also be suitable. For example, mounting angles of 55°, 35°, or 15° with respect to the rotational axis may be suitable depending upon the desired field of view.

The transducer housing 206, to which the transducer subassembly 216 is attached, includes a proximal section 222 secured to the drive shaft 204, a tubular waist section 224, and a tubular distal section 226. The distal section 226 includes a distal opening 228 bounded by a wall section 230 and a wall section 232. The wall section 230 is angled with respect to the rotational axis RA and may, for example, be angled at the mounting angle MA. The wall section 232 may be generally transverse to the rotational axis RA. The distal section 226 has an outer diameter D1.

In use, as configured, the transducer subassembly 216 produces a forward-imaging ultrasound beam 234 propagating generally perpendicular to the face 220 of the transducer subassembly 216. The beam 234 passes through the distal opening 228 of the transducer housing 206 and propagates distally from the catheter system 200 into a vascular region distal (i.e., forward) of the catheter. After reflecting off of tissue, including blockages or occlusions, located distally of the transducer subassembly 216, an echo beam is detected by the transducer subassembly and sent to a control system for processing and display.

Figure 4:
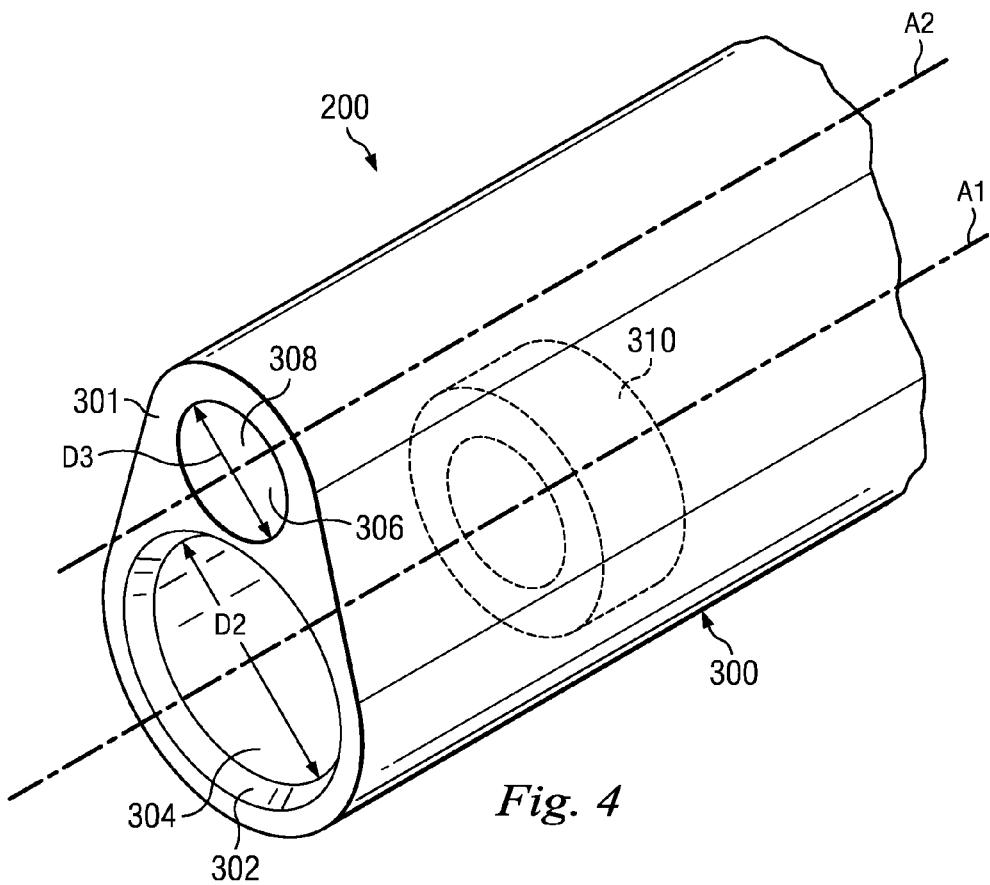
FIG. 4 is an illustration of the distal end of a multi-lumen catheter according to one embodiment of the present disclosure.
Figure 5:
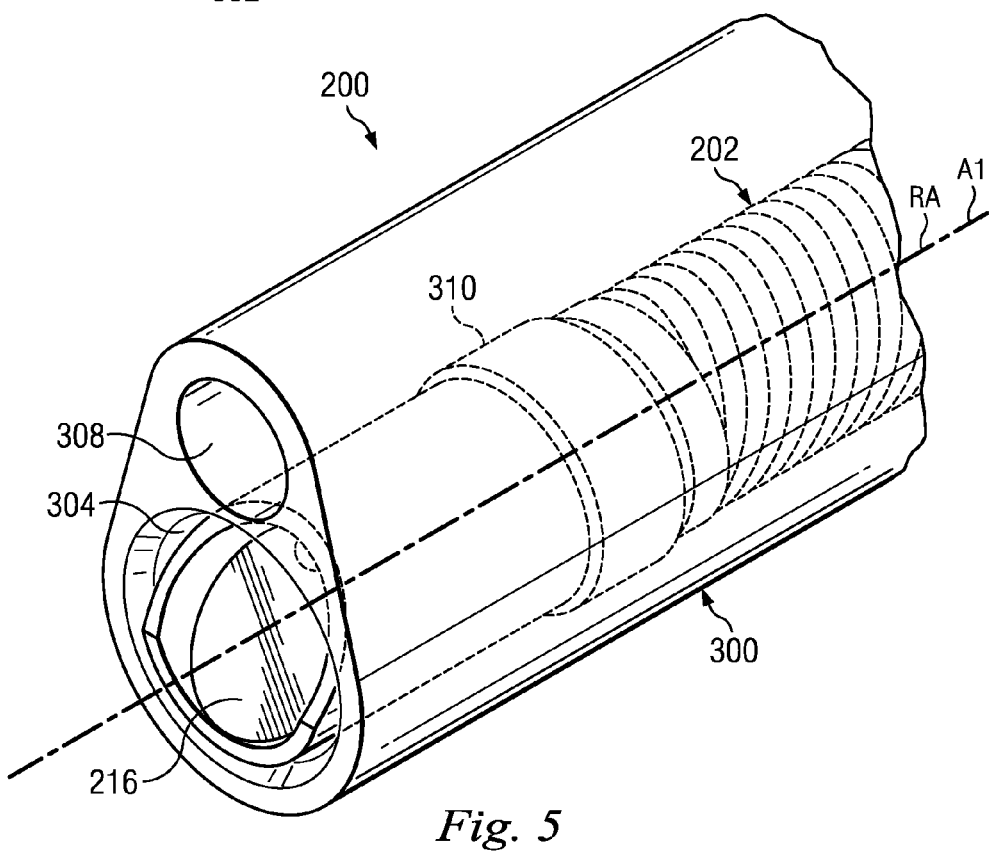
FIG. 5 is an illustration of the distal end of the imaging core of FIGS. 2 & 3 received in the multi-lumen catheter of FIG. 4.

Referring now to FIGS. 4 and 5, the catheter 200 also includes an elongated sheath 300 formed of a flexible, biologically compatible material which may include metals, plastics, and/or ceramics. Because the ultrasonic beam 234 will propagate through a distal opening in the sheath 300 rather than through the sheath 300, as is the case in typical rotational IVUS catheters, it is not essential for the sheath to be formed of a material with an acoustic impedance and sound speed particularly well-suited for conducting the ultrasound beam from the transducer out into the blood vessel with minimal reflection, attenuation, or beam distortion. However, in some embodiments, such a material may still be suitable for the forward looking IVUS catheter 200.

The sheath 300 includes a distal wall 301 having a distal opening 302 in communication with a lumen 304 that extends the length of the sheath 300. The lumen 302 is centered about a longitudinal axis A1 and has a diameter D2 which is sufficiently larger than the outer diameter D1 of the distal section 226 of the transducer housing 206 to permit rotation of the transducer housing and transducer subassembly 216 within the lumen 302. In one embodiment, for example, the diameter D2 of the lumen 302 may be approximately 0.035-0.020 inches. The distal wall 301 extends generally perpendicular to the longitudinal axis A1.

The imaging core 202, including transducer housing 206 and transducer subassembly 216 are inserted into and rotate within the lumen 304. As assembled, the rotational axis RA of the transducer subassembly 216 is generally coincident with the longitudinal axis A1 of the lumen 302. Also as assembled, the wall section 232 of the housing 206 is generally flush with the distal wall 301 to prevent the rotating housing or transducer subassembly 216 from contacting tissue, blood, or other bodily fluids surrounding the sheath 300. In other embodiments, the housing 206 may be slightly extended out of or retracted into the lumen 304. To prevent longitudinal migration of the transducer subassembly 216 within the lumen 304, the housing 206 is rotationally coupled to the sheath 300. In this embodiment, a ring shaped insert 310, is attached around the waist section 224 of the housing 206, such that the waist section 224 rotates with respect to the insert 310. The insert 310 may include a low melt material that is fused to the wall of the lumen 304 and is thus stationary with respect to the lumen 304. In this way, the housing 206 may be rotated within the lumen 304 relative to the insert 310. At the same time, the insert 310 engages housing 206 and proximal section 222 to prevent forward or rearward migration of the housing 206, and therefore the transducer subassembly 216, within the lumen 304.

The sheath 300 also includes an opening 306 in the distal wall 301. The opening 306 is in communication with a lumen 308 that may extend the length of or a partial length of the sheath 300. The lumen 308 may be sized to receive a guide wire 350 (See FIG. 6) or a wire for conducting a therapeutic procedure. For example, a lumen of approximately 0.017 inches may be used with a 0.014 inch wire, and a lumen of approximately 0.020 inches may be used with a 0.018 inch wire. Generally the diameter D3 may be smaller than the diameter D2, but in some embodiments may be larger.

Figure 6:
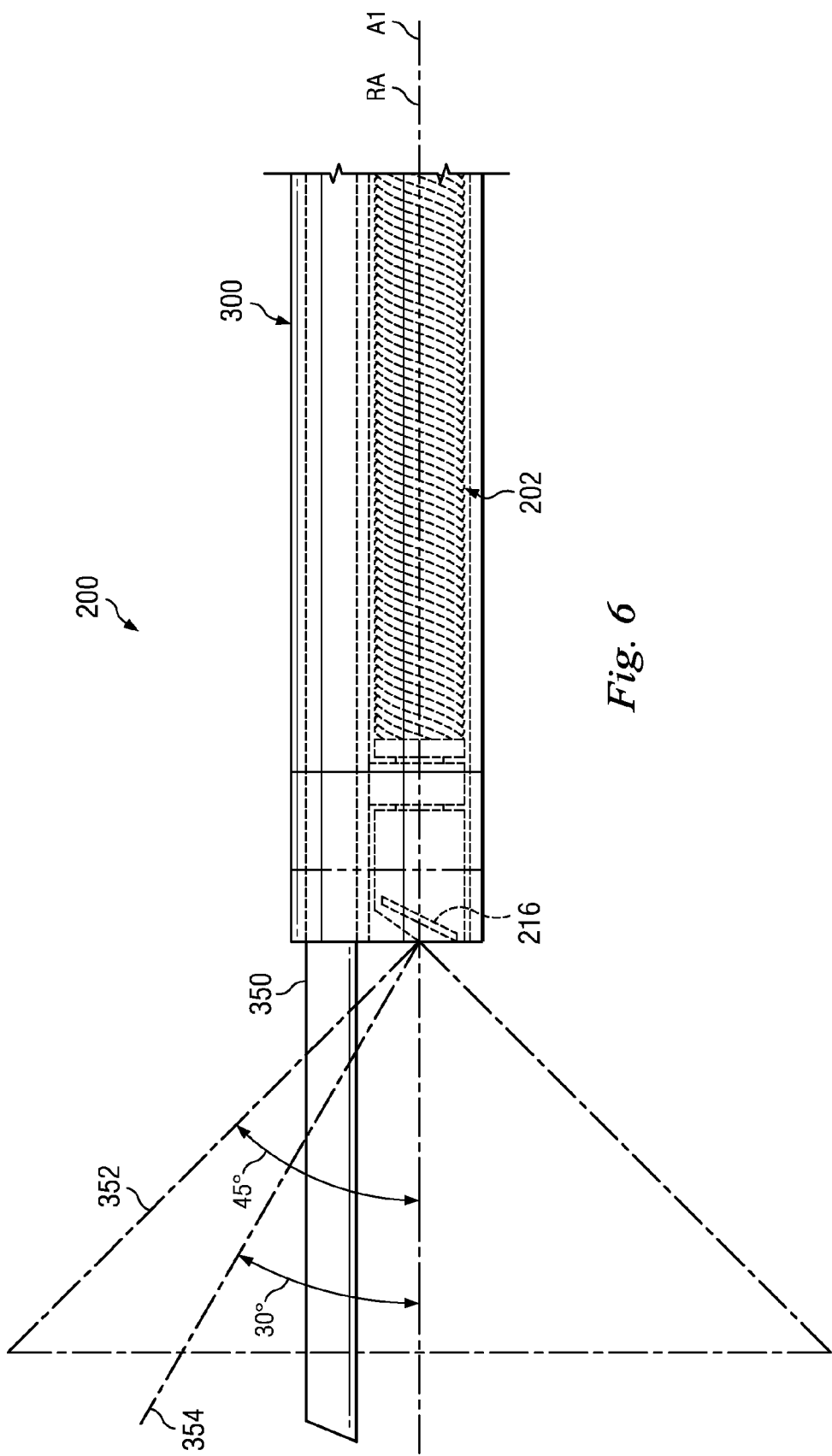
FIG. 6 is a side view of a distal end of a multi-lumen catheter and imaging core illustrating an imaging cone generated by the transducer subassembly according to multiple embodiments of the present disclosure.

FIG. 6 illustrates the imaging core 202 assembled within the sheath 300, with a guide wire 350 extending from the lumen 308 of the sheath. In use, the imaging core 202 is activated to rotate about the rotational axis RA, which causes the transducer subassembly 216 to rotate and produce an imaging cone 352. The imaging cone 352 is a 45° imaging cone generated by the rotation of transducer subassembly 216 angled at a mounting angle MA of 45°. In an alternative embodiment, a transducer subassembly may be mounted at mounting angle MA of 30° to produce a 30° imaging cone 354. In other alternatives, the transducer subassembly may be mounted at other angles, for example 55°, 35°, 25°, or 15° to generate imaging cones of corresponding sizes. In still other alternatives, the mounting angle may be variable and may be adjusted by an operator prior to or during an imaging procedure.

Figure 7:
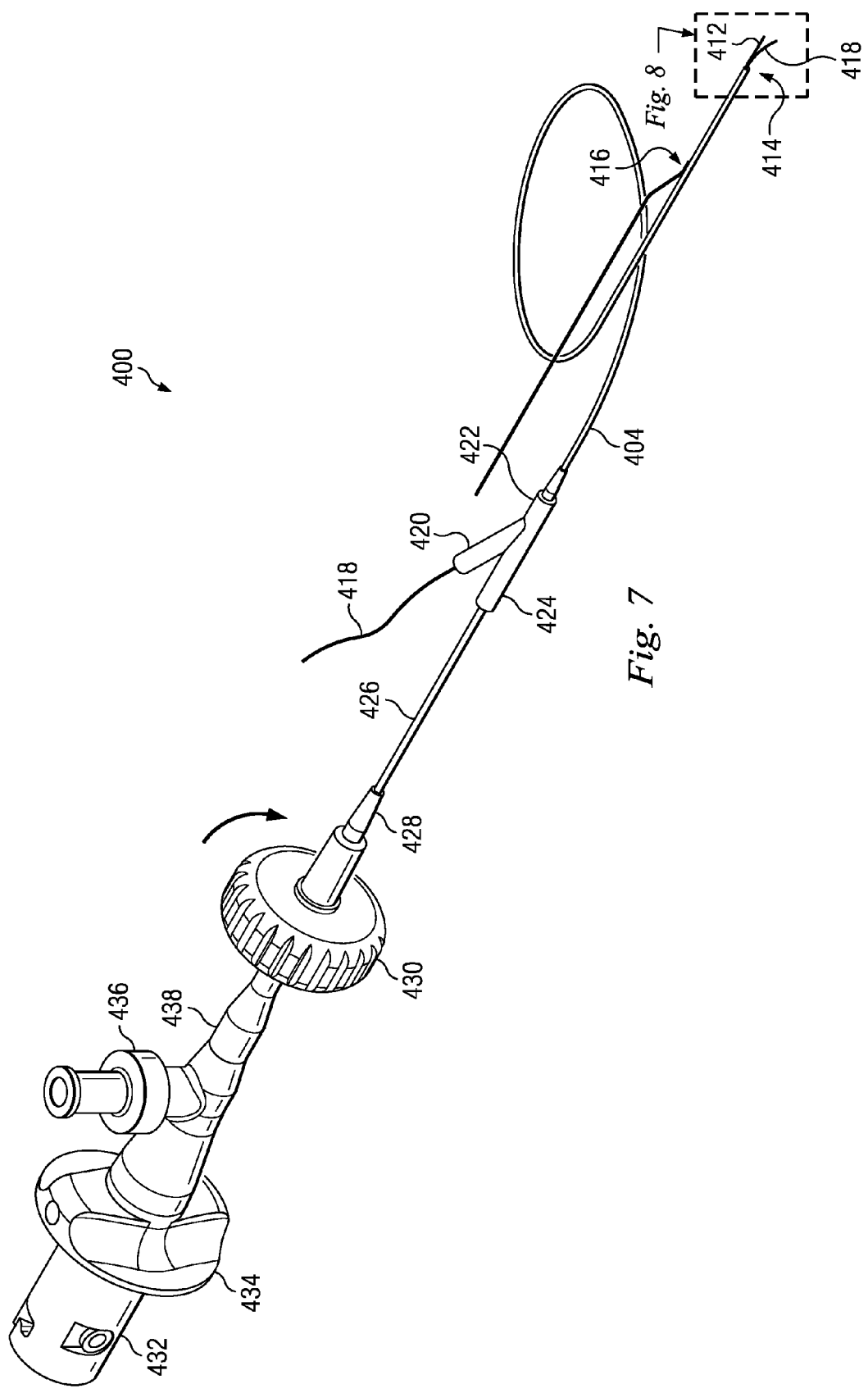
FIG. 7 is an illustration of an IVUS catheter system according to one embodiment of the present disclosure.
Figure 8:
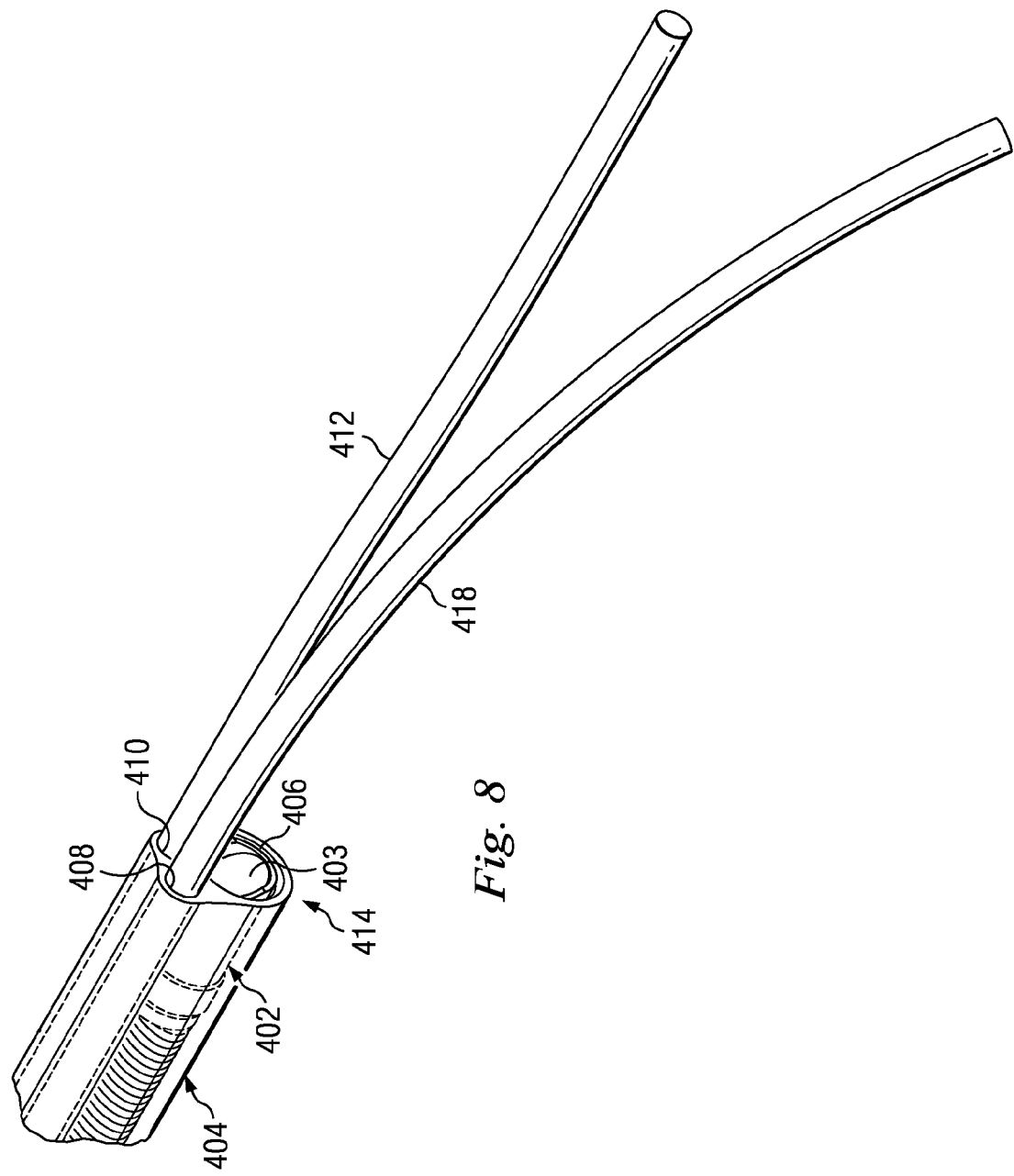
FIG. 8 is an illustration of a distal end of the IVUS catheter system of FIG. 7.
Figure 9:
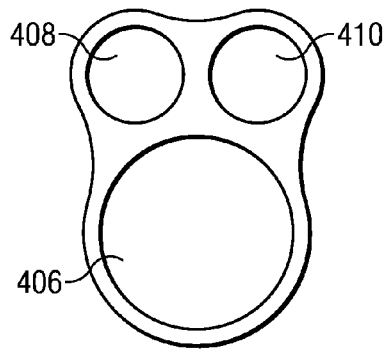
FIG. 9 is an end view of the multi-lumen catheter of the system of FIG. 7.

FIGS. 7 and 8 illustrate an IVUS catheter system 400 according to another embodiment of the present disclosure, with FIG. 8 illustrating in greater detail the distal end portion of the system. The system 400 includes an imaging core 402 with a transducer subassembly 403. The imaging core 402 and the transducer subassembly 403 are the same or substantially similar to the forward-looking imaging core 202 and transducer subassembly 216, previously described. The system 400 also includes a multi-lumen sheath 404 (shown in cross-section in FIG. 9) which is similar to sheath 300, but includes three lumens 406, 408, 410 rather than two. The imaging core 402 extends through and is rotatable within the lumen 406, as previously described for imaging core 202.

Lumens 408, 410 are arranged generally adjacent to each other on a common side of the lumen 406. A guide wire 412 extends through lumen 410. The lumen 410 extends between a distal end 414 of the sheath 404 and a medial opening 416 through which the guide wire 412 extends. This type of catheter structure is a "rapid exchange" (RX) catheter. In alternative embodiments, an "over-the-wire" (OTW) catheter structure may be used.

OTW catheters have a lumen that extends inside the entire length of the catheter into which a guide wire can be inserted. With RX catheters, the guide wire only enters into the catheter body near its distal end, instead of entering at the proximal-most end, and extends inside the catheter body to the distal most end of the catheter where it exits.

There are advantages and disadvantages to both designs. The OTW catheters allow easy exchange of guide wires should additional catheter support, from a stiffer guide wire, or a change in the shape or stiffness of the guide wire tip be necessary. The RX catheters allow the operator to more rapidly change from one catheter to another while leaving the guide wire in place, thereby preserving the placement of the guide wire distal tip, which may have been difficult to achieve. Although "standard" length (typically approximately 190 cm) guide wires usually have a proximal extension capability built in (extending the overall length to approximately 300 cm), the use of these accessories is cumbersome and can require two sterile operators.

Typically, about 190 cm guide wires are required to span a vessel from the most distal anatomy that the interventionalist or operator wishes to treat to the point where the guide catheter, enters the patient's body. The entry point may be located, for example, at the femoral artery in a patient's groin, or on occasion, the radial artery in a patient's arm. If the catheter being loaded over the guide wire is an OTW catheter, the guide wire must be long enough so that the entire length of the OTW catheter can be slid over the proximal end of the guide wire and yet there remain some length of the guide wire exposed where it enters the patient's body. That is, the guide wire for an OTW catheter must be approximately twice as long as one that is to be used only with RX catheters, because it must simultaneously accommodate both the length inside the patient's body and the length of the OTW catheter. Further, the "threading" of the OTW catheter over the distal or proximal end of the guide wire may be time consuming, and the added length of the guide wire can be cumbersome to handle while maintaining sterility.

Since the RX design catheters typically have the guide wire running inside them for only the most distal approximately 1 cm to approximately 30 cm, the guide wire employed need only have a little more than the required approximately 1 cm to 30 cm after it exits the patient's body. While the loading of an approximately 140 cm OTW catheter over an approximately 280 cm to 300 cm guide wire is time consuming and tedious, loading the distal approximately 10 cm of an RX catheter over a shorter guide wire is easily done.

However, OTW catheters may track the path of the guide wire more reliably than RX catheters. That is, the guide wire, acting as a rail, prevents buckling of the catheter shaft when it is pushed forward from its proximal end over the guide wire. RX catheters can, however, given a sufficiently wide target site, such as a sufficiently wide artery, and a sufficiently tortuous guide wire path, buckle as they are advanced along the guide wire by pushing on the proximal end of the catheter. In addition, when an RX catheter is withdrawn from a patient, the RX portion can pull on the guide wire and cause the guide wire to buckle near the point that it exits the proximal end of the RX channel.

Referring again to FIGS. 7, 8, and 9, the lumen 408 may be sized for receipt and passage of an elongated flexible shaft or wire 418 carrying an instrument for conducting a therapeutic procedure. For example, the shaft 418 may carry an instrument for reducing artery or vessel blockages, delivering a stent, conducting a biopsy, performing an ablation, delivering an aneurysm graft, conducting an embolization procedure, or draining fluid. The shaft 418 is inserted into the lumen 408 of the sheath 404 via a port 420 of an adaptor 422. The adaptor 422 further includes a port 424 connected to a single-lumen catheter 426. The sheath 404 is coupled via an adaptor 428 to a control knob 430. Rotating the control knob 430 rotates the sheath 404 relative to the interface module and the imaging core 402. Rotation of the sheath 404 allows a user to control the physical location of the guide wire or procedural wire and thus control the position of the image of the guide wire or procedural wire in the resulting IVUS image. In this way, the image of the wires 412, 418 may be moved out of the way of an area requiring analysis or moved into an area of interest to serve as a landmark.

The imaging core 402 is terminated at a proximal end by a rotational interface 432 providing electrical and mechanical coupling to an interface module (See FIG. 1). The IVUS system 400 further includes a hub 434 that supports the rotational interface 432 and provides a bearing surface and a fluid seal between the rotating and non-rotating elements of the catheter assembly. The hub 434 includes a luer lock flush port 436 through which saline may be injected. Saline may provide a biocompatible lubricant for the rotating imaging core 402. The hub 434 is coupled by a tapered adaptor 438 to the control knob 430.

Figure 10:
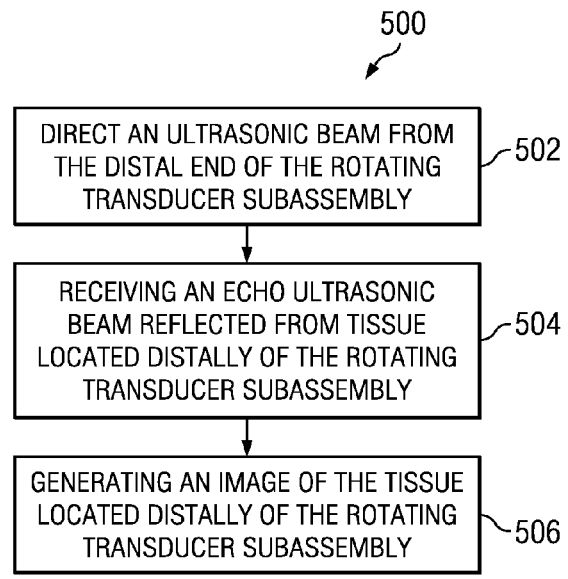
FIG. 10 is a flowchart describing a method of using an IVUS catheter system.

Unlike traditional rotational IVUS catheters, the IVUS catheter system 400 is able to transmit and receive ultrasonic signals with a forward facing transducer subassembly 403 that transmits and receives through an open distal end 414 of the sheath 404, rather than a traditional transducer subassembly that transmits generally perpendicular to the axis of rotation, through a wall of the surrounding catheter. FIG. 10 is a flowchart 500 describing a method of using the catheter system 400. Prior to the implementation of this method, the imaging core 402 is inserted into the sheath 404, and the sheath is guided along a patient's lumen tissue, such as an artery or blood vessel. The sheath 404 is guided, along the guide wire 412, until the tissue to be imaged is positioned distally of the distal end of the sheath. At step 502, an ultrasonic beam is emitted from the transducer subassembly 403 and directed through the distal opening of the sheath 404. The transducer subassembly 403 is rotated about the rotational axis of the imaging core 402 at a rotational speed of approximately 1800 RPM. Slower or faster speeds may also provide effective imaging. The ultrasonic beam encounters the tissue, including any blockages or occlusions, located distally of the sheath. At step 504, a reflected ultrasonic echo is received by the transducer subassembly 403. At step 506, an image of the tissue located distally of the sheath is generated on a display. Because the guide wire 412 or the procedural wire 418 may be visible in the generated image, a user may rotate the control knob 430 to rotate the sheath 404 relative to the interface module. In doing so, the location of the wires 412, 418 in the generated image may be rotated either away from an area of interest to reduce obstruction of view or into an area of interest to serve as a referencing landmark. The imaging procedure may occur before, during, and/or after a procedure conducted with the procedural wire 418. As compared to traditional IVUS, the forward looking IVUS provides continuous imaging.

Figure 11:
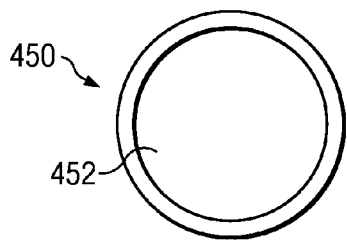
FIG. 11 is an end view of a single-lumen catheter according to one embodiment of the present disclosure.
Figure 12:
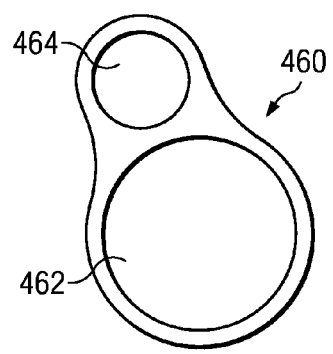
FIGS. 12-14 are end-views of multi-lumen catheters according to alternative embodiments of the present disclosure.
Figure 13:
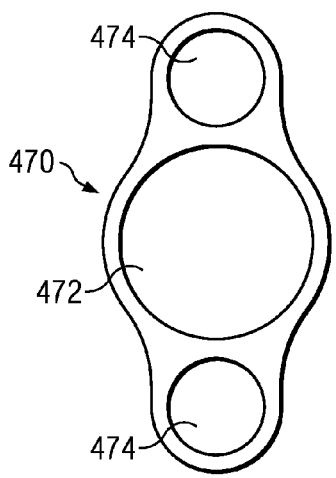
Figure 14:
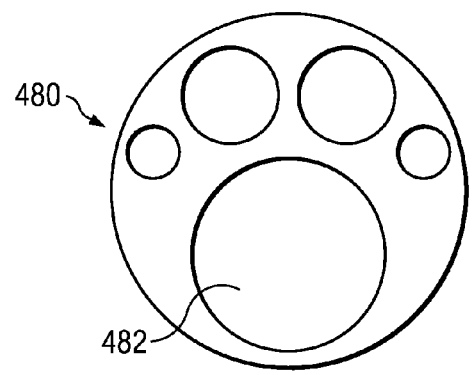

In alternative embodiments, rotating imaging cores with forward looking transducer subassemblies may rotate within open ended catheters of a variety of configurations. As shown in FIG. 11, a catheter sheath 450 has a single imaging lumen 452 sized to receive a rotatable imaging core. As shown in FIG. 12, a catheter sheath 460 has a dual lumen structure with an imaging lumen 462 sized to receive a rotatable imaging core and lumen 464 sized to receive a guide wire or procedure instrument. As shown in FIG. 13, a catheter sheath 470 has a triple lumen structure with an imaging lumen 472 sized to receive a rotatable imaging core. A set of lumens 474, 476 are disposed on opposite sides of the imaging lumen 472 from each other. One lumen of the set of lumens 474, 476 may be used to receive a guide wire, while the other is used to receive a procedure instrument. As shown in FIG. 14, a catheter sheath 480 has a multi-lumen structure with an imaging lumen 482 sized to receive a rotatable imaging core. A lumen 484 is sized to receive a guide wire. A lumen 486 extends adjacent to the lumen 484 and is sized to receive a procedure instrument. A set of lumens 488, 490 are disposed on opposite sides of the imaging lumen 482 from each other. The lumens 488, 490 may have a smaller diameter than lumens 482, 484, 486, and may be sized to receive steering wires that allow a user to manipulate the shape and/or direction of the catheter sheath 480 from a proximal control location. In another alternative embodiment, more lumens may extend adjacent to the main imaging core lumen. Additional lumen may be used for example, to receive additional procedural instruments or to receive additional steering wires. Although the previously described embodiments have included open-ended catheter sheaths, in an alternative embodiment, the catheter sheath may have a closed-end formed of a material that has an acoustic impedance and a sound speed well-suited for conducting an ultrasound beam from a forward-imaging transducer, with minimal reflection, attenuation, or beam distortion. In this alternative, an acoustic lens may be used.

One or more elements in embodiments of the invention may be implemented in software to execute on a processor of a computer system such as control system 106. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, Intranet, etc.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A system for imaging a vessel of a patient, the system comprising:
   an elongated sheath having a proximal and a distal end and including a flexible body with a first lumen in communication with a distal opening at the distal end; and
   an imaging core disposed within the first lumen, the imaging core including a housing sized to extend within the first lumen and a transducer subassembly disposed within the housing, the transducer subassembly adapted to transmit a beam, distally of the elongated sheath, through the distal opening of the first lumen and a distal end of the housing, wherein the imaging core is rotatable within the first lumen about a longitudinal axis of the elongated sheath, wherein the distal end of the housing is bounded by a first wall section disposed perpendicular to the axis of rotation of the imaging core, and a second wall section extending at a first oblique angle with respect to the first wall section and the axis of rotation of the imaging core, wherein the transducer subassembly includes a planar face extending at a second oblique angle with respect to the axis of rotation of the imaging core, and wherein the planar face is disposed within the distal opening at the distal end of the elongated sheath such that the planar face defines at least a portion of a distal-most tip, wherein the distal end of the housing is aligned with the transducer subassembly such that first wall section does not extend distally beyond the planar face of the transducer subassembly.

2. The system of claim 1 wherein the oblique angle is 45 degrees.

3. The system of claim 1 further including a ring-shaped insert fixedly coupled within the first lumen and rotatably coupled to the imaging core, wherein longitudinal motion of the imaging core relative to the sheath is limited by the insert.

4. The system of claim 1 wherein the flexible body includes a second lumen sized to receive a guide wire.

5. The system of claim 4 wherein the second lumen has a proximal opening between the proximal and distal ends of the elongated sheath and a distal opening at the distal end of the sheath.

6. The system of claim 1 wherein the flexible body includes a third lumen.

7. The system of claim 6 further comprising a steering wire disposed in the third lumen.

8. The system of claim 6 further comprising a shaft of a procedural instrument disposed in the third lumen.

9. The system of claim 1 further including a control knob for rotating the elongated sheath relative to the imaging core.

10. The system of claim 1 wherein the beam is an ultrasound beam.

11. The system of claim 1 wherein the transducer subassembly is rotatable within the first lumen as bodily fluids from the vessel of the patient are received in the first lumen and engage with the transducer subassembly.

12. The system of claim 1 wherein the first oblique angle is substantially equal to the second oblique angle.

13. The system of claim 1 wherein the first oblique angle is not equal to the second oblique angle.

14. A method of imaging a vessel of a patient, the method comprising:
providing an elongated sheath having a proximal and a distal end and including a flexible body with a first lumen in communication with a distal opening at the distal end;
providing a transducer subassembly disposed within a housing sized to extend within the first lumen, a distal end of the housing bounded by a first wall section disposed perpendicular to the axis of rotation of the imaging core, and a second wall section extending at a first oblique angle with respect to the first wall section and the axis of rotation of the transducer subassembly, wherein providing a transducer subassembly includes providing a transducer element with a planar face extending at a second oblique angle with respect to the axis of rotation of the transducer subassembly, the planar face being disposed within the distal opening at the distal end of the elongated sheath such that the planar face defines at least a portion of a distal-most tip, wherein the distal end of the housing is aligned with the transducer subassembly such that first wall section does not extend distally beyond the planar face of the transducer subassembly;
rotating the transducer subassembly within the first lumen about a longitudinal axis of the elongated sheath while directing a beam from the distal opening of the first lumen and a distal end of the housing; and
receiving a reflected beam through the distal opening.

15. The method of claim 14 further comprising generating an image of an area of the vessel distal of the distal end of the elongated sheath.

16. The method of claim 14 wherein the oblique angle is 45 degrees.

17. The method of claim 14 wherein providing the transducer subassembly includes rotatably coupling the transducer subassembly to the elongated sheath.

18. The method of claim 14 wherein the flexible body includes a second lumen, the method further comprising providing a guide wire disposed within the second lumen.

19. The method of claim 18 wherein the second lumen has a proximal opening between the proximal and distal ends of the elongated sheath and a distal opening at the distal end of the sheath.

20. The method of claim 14 wherein the flexible body includes a third lumen.

21. The method of claim 20 further comprising receiving a steering wire in the third lumen.

22. The method of claim 20 further comprising receiving a shaft of a procedural instrument in the third lumen.

23. The method of claim 14 further including responsive to manipulation of a control knob, rotating the elongated sheath relative to the transducer subassembly.

24. The method of claim 14 wherein the beam is an ultrasound beam.

25. The method of claim 14 wherein rotating the transducer subassembly within the first lumen while directing a beam from the distal opening includes receiving bodily fluids from the vessel of the patient into engagement with the transducer subassembly.

* * * * *